United States Patent
Pilly et al.

(10) Patent No.: US 10,046,162 B1
(45) Date of Patent: Aug. 14, 2018

(54) TRANSCRANIAL INTERVENTION TO WEAKEN TRAUMATIC MEMORIES

(71) Applicant: HRL Laboratories, LLC, Malibu, CA (US)

(72) Inventors: Praveen K. Pilly, West Hills, CA (US); Michael D. Howard, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/072,353

(22) Filed: Mar. 16, 2016

Related U.S. Application Data (60) Provisional application No. 62/210,890, filed on Aug. 27, 2015, provisional application No. 62/210,907, filed on Aug. 27, 2015, provisional application No. 62/247,435, filed on Oct. 28, 2015.

(51) Int. Cl.
*A61N 1/36* (2006.01)
*A61N 1/04* (2006.01)

(52) U.S. Cl.
CPC ....... *A61N 1/36025* (2013.01); *A61N 1/0456* (2013.01); *A61N 1/0484* (2013.01)

(58) Field of Classification Search
CPC .................................................. A61N 1/36025
USPC ............................................................ 607/45
See application file for complete search history.

(56) References Cited

U.S. PATENT DOCUMENTS

| | | | |
|---|---|---|---|
| 8,716,778 B2 | 5/2014 | Bikson et al. | |
| 9,116,835 B1* | 8/2015 | Smyth | A61B 5/0476 |
| 9,370,658 B2* | 6/2016 | Neuvonen | A61N 1/36014 |
| 2009/0319002 A1* | 12/2009 | Simon | A61N 1/0408 |
| | | | 607/45 |
| 2012/0046531 A1* | 2/2012 | Hua | A61B 5/6865 |
| | | | 600/317 |
| 2012/0245653 A1 | 9/2012 | Bikson et al. | |
| 2012/0265261 A1* | 10/2012 | Bikson | A61N 1/36025 |
| | | | 607/2 |
| 2015/0025590 A1* | 1/2015 | Cheng | A61N 1/36021 |
| | | | 607/3 |

(Continued)

OTHER PUBLICATIONS

Tremblay, Sara, Jean-François Lepage, Alex Latulipe-Loiselle, Felipe Fregni, Alvaro Pascual-Leone, and Hugo Théoret. "The Uncertain Outcome of Prefrontal TDCS." Brain Stimulation 7.6 (2014): 773-83. Web.*

(Continued)

*Primary Examiner* — Allen Porter, Jr.
(74) *Attorney, Agent, or Firm* — Tope-McKay & Associates (57) ABSTRACT

Described is a system for weakening traumatic memories using transcranially-applied electro-stimulation. The system uses a recording of spatiotemporally distributed brain activity of a human subject experiencing a traumatic memory to generate a traumatic pattern. Additionally, the system uses a recording of spatiotemporally distributed brain activity of the human subject experiencing a non-traumatic memory to generate an antidote pattern. A required transcranially-applied electro-stimulation is determined to recreate the antidote pattern to block consolidation and reconsolidation of the traumatic memory in the human subject.

21 Claims, 8 Drawing Sheets

(56) References Cited

U.S. PATENT DOCUMENTS

2016/0228702 A1* 8/2016 Kempe .............. A61N 1/36025

OTHER PUBLICATIONS

Segrave, R.a., S. Arnold, K. Hoy, and P.b. Fitzgerald. "Concurrent Cognitive Control Training Augments the Antidepressant Efficacy of TDCS: A Pilot Study." Brain Stimulation 7.2 (2014): 325-31. Web.*

Castano-Candamil, Ssebastian et al. "Solving the EEG Inverse Problem Based on Space-Time-Frequency Structured Sparsity Constraints." NeuroImage 118 (2015) 598-612. Web.*

Nader K, Schafe GE, Le Deux JE. Fear memories require protein synthesis in the amygdala for reconsolidation after retrieval. Nature. 2000; 406: pp. 722-726.

Dudai Y. The neurobiology of consolidations, or, how stable is the engram? Annu. Rev. Psychol. 2004; 55: pp. 51-86.

Squire LR, Alvarez P. Retrograde amnesia and memory consolidation: a neurobiological perspective Curr. Opin. Neurobiol. 1996; 5: pp. 169-177.

Foa EB. Social anxiety disorder treatments: psychosocial therapies. J. Clin. Psychiatry, 2006: 67 Suppl 12: pp. 27-30.

Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.

Bustos SG, Maldonado H, Molina VA. Midazolam disrupts fear memory reconsolidation. Neuroscience. 2006; 139: pp. 831-842.

Sandrini M, Censor N, Mishee J, Cohen LG. Causal Role of Prefrontal Cortex in Strengthening of Episodic Memories through Reconsolidation. Curr. Biol. 2013; 23: pp. 2181-2184.

Soterix Medical Website. High Definition-transcranial Direct Current Stimulation (HD-tDCS) [Internet]. Available from: http://soterixmedical.com/hd-tdcs, downloaded Aug. 8, 2016. pp. 1-13.

Chan JCK, LaPaglia JA. Impairing existing declarative memory in humans by disrupting reconsolidation. Proc. Natl. Acad. Sci. 2013;110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.

Euston DR, Gruber AJ, McNaughton BL. The rote of medial prefrontal cortex in memory and decision making. Neuron. 2012; 76: pp. 1057-1070.

Ji D, Wilson MA. Coordinated memory replay in the visual cortex and hippocampus during sleep. Nat. Neurosci. 2007; 10: pp. 100-107.

Wolters CH, Anwancler A, Tricoche X, Weinstein D. Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.

Dmochowski JP, Datta A, Bikson M, Su Y, Parra LC. Optimized multi-electrode stimulation increases focality and intensity at target. J. Neural Eng. 2011; 8:pp. 046011-1-046011-16.

Grech, R., Cassar, T., Muscat, J., Camilleri, K.P., Fabri, S.G., Zervakis, M., Xanthopoulos, P., Sakkalis, V. and Vanrumste, B., 2008. Review on solving the inverse problem in EEG source analysis. Journal of neuroengineering and rehabilitation, 5(1), pp. 1-33.

Tucker DM. Spatial sampling of head electrical fields: the geodesic sensor net. Electroencephalogr. Clin. Neurophysiol, 87: pp. 154-163, 1993.

Michel C., Murray MM. Towards the utilization of EEG as a brain imaging tool, NeuroImage 61 (2012), pp. 371-385.

Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.

Dmochowski JP, Datta A, Bikson M, Su Y, Parra LC. Optimized multi-electrode stimulation increases locality and intensity at target. J. Neural Eng., 8:046011, 2011, pp. 1-16.

Jones DK and Leemans A, "Diffusion Tensor Imaging", Methods in Molecular Biology 711: pp. 127-144, 2011.

Ramírez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.

McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.

Marshall L, Helgadóttir H, Mölle M, Born J. Boosting slow oscillations during sleep potentiates memory. Nature. 2006;444: pp. 610-613.

Javadi AH, Walsh V. Transcranial direct current stimulation (tDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science. 2007;315: pp. 1426-1429.

Rudoy JD, Voss JL, Westerberg CE, Paller KA. Strengthening Individual Memories by Reactivating Them During Sleep. Science. 2009;326: p. 1079.

Bendor D, Wilson MA. Biasing the content of hippocampal replay during sleep. Nat. Neurosci. 2012;15: pp. 1439-1444.

Euston DR, Gruber AJ, McNaughton BL. The role of medial prefrontal cortex in memory and decision making. Neuron. 2012;76: pp. 1057-1070.

Ji D, Wilson MA. Coordinated memory replay in the visual cortex and hippocampus during sleep. Nat. Neurosci. 2007;10: pp. 100-107.

Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007; 318 (5853): pp. 1147-1150.

The SenseWear armband as a Sleep Detection Device [Internet]. [cited Nov. 23, 2014]. pp. 1-9. Available from: http://www.bodymedia.com/Professionals/Whitepapers/The-SenseWear-armband-as-a-Sleep-Detection-Device?hence=.

Edmund Rolls, "The mechanisms for pattern completion and pattern separation in the hippocampus," Front Syst Neurosci. Oct. 2013; vol. 7: Article 74, pp. 1-21.

Thomas J. McHugh, et al., "Dentate Gyrus NMDA Receptors Mediate Rapid Pattern Separation in the Hippocampal Network," Science, vol. 317, (Jul. 2007); pp. 94-99.

Jesse Rissman, et al., "Distributed representations in memory: Insights from functional brain imaging," Annu Rev Psychol. 2012; 63: pp. 101-128.

Giulio Ruffinia, et al., "Optimization of multifocal transcranial current stimulation for weighted cortical pattern targeting from realistic modeling of electric fields," Neuroimage. Apr. 1, 2014; 89: pp. 216-225.

"An automated pipeline for constructing personalized virtual brains from multimodal neuroimaging data," NeuroImage, vol. 117, Aug. 15, 2015, pp. 343-357.

Krause, M. R., Zanos, T. P., Csorba, B. A., Pilly, P. K., Choe, J., Phillips, M. E., Datta, A., and Pack, C. C. (2017). Transcranial direct (56) References Cited

OTHER PUBLICATIONS current stimulation facilitates associative learning and alters functional connectivity in the primate brain. Current Biology, 27(3), pp. 3086-3096.

* cited by examiner

TRANSCRANIAL INTERVENTION TO WEAKEN TRAUMATIC MEMORIES

CROSS-REFERENCE TO RELATED APPLICATIONS

This is a Non-Provisional Application of U.S. Provisional Patent Application No. 62/210,890 filed Aug. 27, 2015, entitled, "Transcranial Intervention to Weaken Traumatic Memories," the entirety of which is incorporated herein by reference.

This is ALSO a Non-Provisional Application of U.S. Provisional Patent Application No. 62/210,907 filed Aug. 27, 2015, entitled, "Method to Enhance Specific Memories with tCS During Slow-Wave Sleep," the entirety of which is incorporated herein by reference.

This is ALSO a Non-Provisional Application of U.S. Provisional Application No. 62/247,435, filed in the United States on Oct. 28, 2015, entitled, "Mapping Transcranial Signals to Transcranial Stimulation Required to Reproduce a Brain State," the entirety of which is incorporated herein by reference.

BACKGROUND OF INVENTION

(1) Field of Invention

The present invention relates to a system for weakening traumatic memories and, more particularly, to a system for weakening traumatic memories using transcranial stimulation.

(2) Description of Related Art

Traumatic memories are intense, stressful, and emotionally paralyzing. The reconsolidation hypothesis states that when a consolidated memory is recalled, it becomes unstable and susceptible to facilitation or impairment for a discrete period of time, gradually becoming stable again. Prior art methods to impair existing declarative memories in humans by disrupting reconsolidation either use a behavioral re-conditioning paradigm during waking (see the List of Incorporated Literature References, Literature Reference No. 10) or employ drugs that inhibit protein synthesis during or following the experience of a traumatic memory (see Literature Reference No. 11).

Eye movement desensitization and reprocessing (described in Literature Reference No. 5) uses a series of eye and hand movements applied in a specific sequence in a clinical setting. Like cognitive behavioral therapy, it requires appointments with trained therapists to evoke the disturbing memories and administer the treatment.

Often medication, such as Prozac or Zoloft, is prescribed to post-traumatic stress disorder (PTSD) sufferers, but these antidepressants do not treat the causes, only the symptoms, and have the potential for psychological dependence and addiction. Midazolam specifically disrupts reconsolidation (see Literature Reference No. 6), but it is a powerful sedative which can be dangerous.

Prior art transcranial stimulation methods, which use two large electrode pads on the scalp, have already shown an average 150% improvement in long-term memory retention in elderly subjects on a free recall task by stimulation of the pre-frontal cortex (PFC) during reconsolidation following memory recall on day 2 after initial encoding (see Literature Reference No. 7).

While such stimulation methods have been shown to improve memory retention, no such technique has been devised to reduce or otherwise remove memories.

Thus, a continuing need exists for a targeted transcranial neurostimulation system which will cure patients of post-traumatic stress and rid them of disturbing memories without physical risk to the patient.

SUMMARY OF THE INVENTION

The present invention relates to a system for weakening traumatic memories and, more particularly, to a system for weakening traumatic memories using transcranial stimulation. The system comprises one or more processors and a memory having instructions such that when the instructions are executed, the one or more processors perform multiple operations. The system uses at least one recording of spatiotemporally distributed brain activity of a human subject experiencing a traumatic memory to generate at least one traumatic pattern. The system then uses at least one recording of spatiotemporally distributed brain activity of the human subject experiencing a non-traumatic memory to generate an antidote pattern. A required transcranially-applied electro-stimulation is computed to recreate the antidote pattern to block consolidation and reconsolidation of the traumatic memory in the human subject.

In another aspect, the human subject indicates when a traumatic memory has begun and initiates the at least one recording of spatiotemporally distributed brain activity sensed by a plurality of sensors.

In another aspect, the traumatic memory is sensed by a high-resolution sensor array distributed over the head of the human subject.

In another aspect, a plurality of traumatic memories are recorded to determine a representative traumatic pattern. A plurality of non-traumatic memories are recorded to determine a representative antidote pattern. The representative traumatic pattern and the representative antidote pattern are used to train a classifier to recognize the at least one traumatic pattern.

In another aspect, the system recognizes, with the trained classifier, a neocortical replay associated with the at least one traumatic pattern while the human subject is asleep. Therapy is initiated automatically, applying transcranial electro-stimulation corresponding to a compressed version of the antidote pattern at a set of electrodes positioned on the human subject's scalp.

In another aspect, transcranial electro-stimulation corresponding to an uncompressed version of the antidote pattern is applied at a set of electrodes positioned on the human subject's scalp when the human subject initiates therapy upon experiencing a traumatic memory while awake.

In another aspect, the antidote pattern is applied using a transcranial stimulation cap worn by the human subject.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for weakening traumatic memories and, more particularly, to a system for weakening traumatic memories using transcranial stimulation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

Before describing the invention in detail, first a list of cited literature references used in the description is provided. Next, a description of various principal aspects of the present invention is provided. Finally, specific details of the present invention are provided to give an understanding of the specific aspects.

(1) LIST OF INCORPORATED LITERATURE REFERENCES

The following references are cited and incorporated throughout this application. For clarity and convenience, the references are listed herein as a central resource for the reader. The following references are hereby incorporated by reference as though fully included herein. The references are cited in the application by referring to the corresponding literature reference number, as follows:

1. Nader K, Schafe G E, Le Doux J E. Fear memories require protein synthesis in the amygdala for reconsolidation after retrieval. Nature. 2000; 406:722-6.
2. Dudai Y. The neurobiology of consolidations, or, how stable is the engram? Annu. Rev. Psychol. 2004; 55:51-86.
3. Squire L R, Alvarez P. Retrograde amnesia and memory consolidation: a neurobiological perspective. Curr. Opin. Neurobiol. 1995; 5:169-77.
4. Foa E B. Social anxiety disorder treatments: psychosocial therapies. J. Clin. Psychiatry. 2006; 67 Suppl 12:27-30.
5. Seidler G H, Wagner F E. Comparing the efficacy of EMDR and trauma-focused cognitive-behavioral therapy in the treatment of PTSD: a meta-analytic study. Psychol. Med. 2006; 36: 1515-22.
6. Bustos S G, Maldonado H, Molina V A. Midazolam disrupts fear memory reconsolidation. Neuroscience. 2006; 139:831-42.
7. Sandrini M, Censor N, Mishoe J, Cohen L G. Causal Role of Prefrontal Cortex in Strengthening of Episodic Memories through Reconsolidation. Curr. Biol. 2013; 23:2181-4.
8. Bikson M. Apparatus and method for focal electrical stimulation. 2010.
9. Bikson M, Datta A, Parra L C, Dmochowski J, Su Y. Neurocranial electrostimulation models, systems, devices, and methods. 2012.
10. Chan J C K, LaPaglia J A. Impairing existing declarative memory in humans by disrupting reconsolidation. Proc. Natl. Acad. Sci. 2013; 110:9309-13.
11. Brunet A, Orr S P, Tremblay J, Robertson K, Nader K, Pitman R K. Effect of post-retrieval propranolol on psychophysiologic responding during subsequent script-driven traumatic imagery in post-traumatic stress disorder. J. Psychiatr. Res. 2008; 42:503-6.
12. Euston D R, Gruber A J, McNaughton B L. The role of medial prefrontal cortex in memory and decision making. Neuron. 2012; 76:1057-70.
13. Ji D, Wilson M A. Coordinated memory replay in the visual cortex and hippocampus during sleep. Nat. Neurosci. 2007; 10:100-7.
14. Wolters C H, Anwander A, Tricoche X, Weinstein D, Koch M A, MacLeod R S. Influence of tissue conductivity anisotropy on EEG/MEG field and return current computation in a realistic head model: a simulation and visualization study using high-resolution finite element modeling. NeuroImage. 2006; 30:813-26.
15. Dmochowski J P, Datta A, Bikson M, Su Y, Parra L C. Optimized multi-electrode stimulation increases focality and intensity at target. J. Neural Eng. 2011; 8:046011.
16. Ramirez R, Makeig S. Neuromagnetic source imaging of spatiotemporal brain dynamical patterns using frequency domain independent vector analysis (IVA) and geodesic sparse Bayesian learning (gSBL). Chicago, Ill.: Organization for Human Brain Mapping, 2007.
17. Wong P. Introduction to Brain Topography. New York, N.Y., USA: Plenum Press, 1991.
18. Jones D K and Leemans A, "Diffusion Tensor Imaging", Methods in Molecular Biology 711:127-144, 2011.

(2) PRINCIPAL ASPECTS

The present invention has three "principal" aspects. The first is a system for weakening traumatic memories. The system is typically in the form of a computer system operating software or in the form of a "hard-coded" instruction set. This system may be incorporated into a wide variety of devices that provide different functionalities and may include the relevant sensors and/or stimulators as needed. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
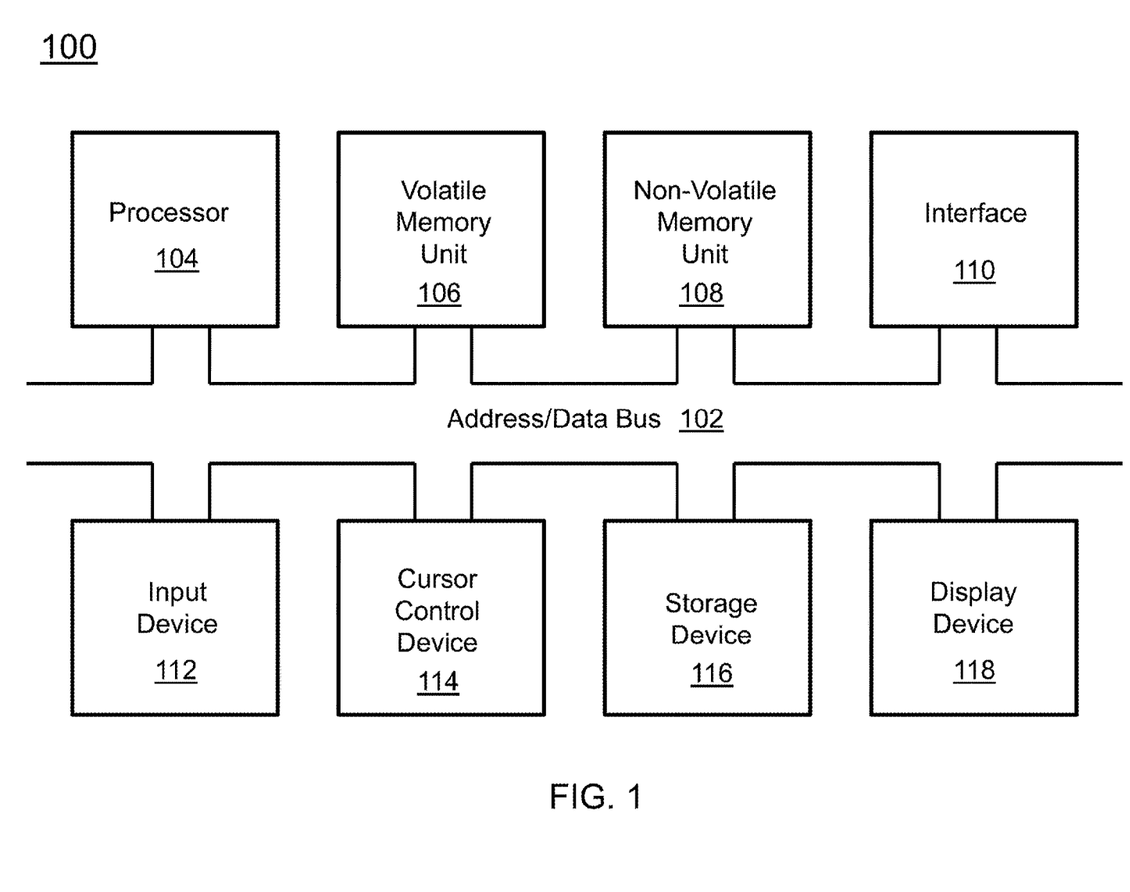
FIG. 1 is a block diagram depicting the components of a system for weakening traumatic memories according to various embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. For example, the input device 112 may include one or more sensors, such as a camera for video or still images, a microphone, or a neural sensor. Other example input devices 112 may include an accelerometer, a GPS sensor, or a gyroscope.

In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
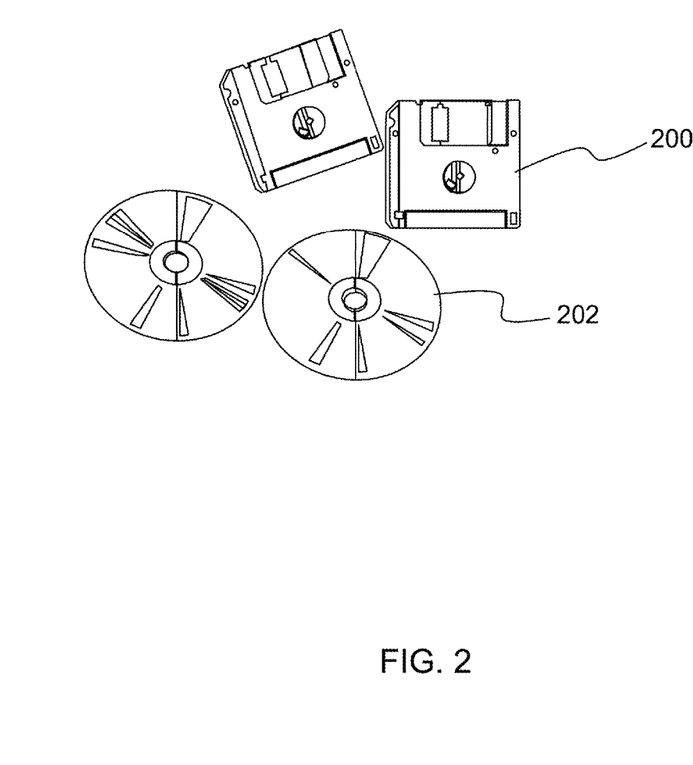
FIG. 2 is an illustration of a computer program product according to various embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) SPECIFIC DETAILS OF THE INVENTION

Traumatic memories are intense, stressful, and emotionally paralyzing. The reconsolidation hypothesis states that when a consolidated memory is recalled, it becomes unstable and susceptible to facilitation or impairment for a discrete period of time, gradually becoming stable again. The system according to some embodiments of the present disclosure will weaken traumatic memories (e.g., post-traumatic stress), by interfering with the reconsolidation process during wake, as well as the subsequent sleep consolidation process (see Literature References No. 2), using targeted, transcranially applied, and electrical stimulation.

Figure 3:
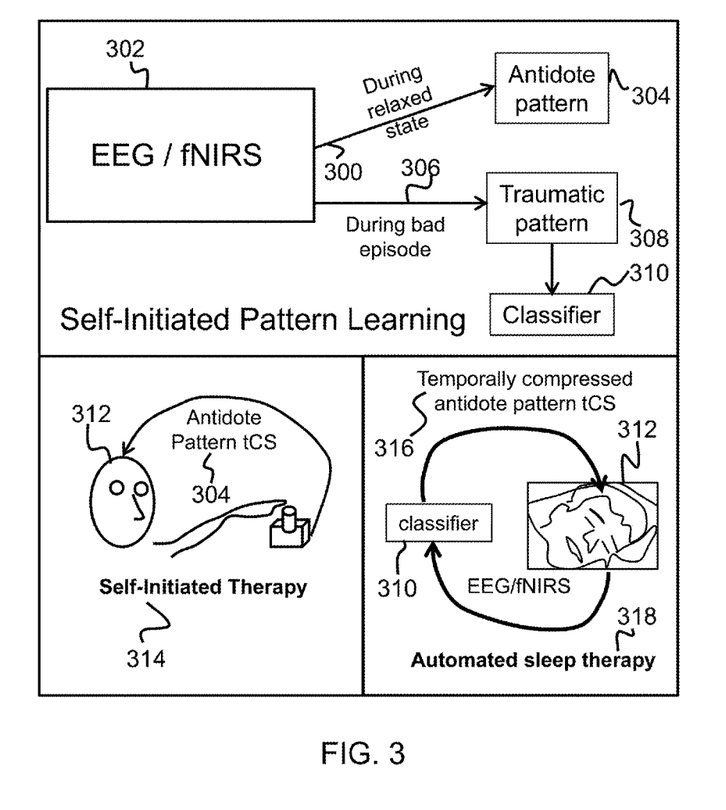
FIG. 3 is an illustration summarizing the basic component of the system for weakening traumatic memories according to various embodiments of the present disclosure.

FIG. 3 illustrates the basic components of the system according to various embodiments of the present disclosure. During a happy, relaxed state 300, spatiotemporally distributed brain activity is recorded from sensors, such as high-resolution electroencephalogram (EEG) and functional near-infrared spectroscopy (fNIRS) 302. This is called the "antidote pattern" 304. When a traumatic memory is relived during a bad episode 306, the antidote pattern 304 can be used to block reconsolidation of the traumatic memory. A traumatic pattern 308 is produced as a result of the bad episode 306. The traumatic pattern 308 is then sent to a classifier 310 for training of the classifier 310. The antidote pattern 304 is applied using a transcranial stimulation cap, which sends low levels of high-definition transcranial current stimulation (tCS) into the brain to recreate the antidote pattern 304 by affecting cell excitability across distributed brain areas. The transcranial stimulation cap comprises multiple electrodes and sensors. As a non-limiting example, the transcranial stimulation cap is fitted with transcranial EEG/fNIRS sensors and HD-tCS electrodes.

The patient 312 can apply this treatment during self-initiated therapy 314, which will feel like no more than a minor tingling sensation. If needed, the negative memory could also be "artificially" triggered to apply the present invention under clinical settings at pre-arranged times. For instance, traumatic memories can be triggered during waking by reliving the event in memory on purpose, which may require the help of a therapist to help the patient. This procedure for using transcranial electrical stimulation to weaken traumatic memories by interrupting their reconsolidation is novel.

Additionally, the system described herein includes a procedure for learning a mapping between a transcranially sensed brain activation pattern and the required transcranially applied stimulation to recreate that pattern (e.g., antidote pattern 304) in the brain. Also described is a procedure for automatically recognizing the cortical replay of a traumatic memory during non-rapid eye movement (REM) sleep (slow-wave sleep in particular), as well as automatically applying a temporally compressed version of the antidote pattern 316 to disrupt a new round of sleep consolidation across the neocortical regions for the traumatic memory recalled during recent wake period. During an episode where the traumatic memory is relived (i.e., during a bad episode 306), spatiotemporally distributed brain activity (via, for instance, EEG and fNIRS 302) is recorded. This is called the "traumatic pattern" 308, and it is used to train classifiers 310 for recognition of its sped-up replay during non-REM sleep.

The targeted transcranial neurostimulation system according to various embodiments can assist in curing a patient of post-traumatic stress and rid the patient of disturbing memories without physical risk. The present invention has goals similar to trauma-focused cognitive behavioral therapy techniques (such as that described in Literature Reference No. 4) that are common in psychological treatment. However, unlike such techniques that require appointments with trained therapists for months or years of sessions, the present invention can be applied any time, throughout the day or night, by an automated system. The patient is treated as he/she goes about their normal routine (not in a clinical session), so therapy can be applied when something triggers the feelings. The patient can get treatment as simply as pushing a button, rather than making an appointment for some future time. For instance, the invention can be implemented in a portable configuration that the user can wear with an activation switch or button on the equipment. Even better, treatment can be applied automatically during sleep.

When a subject relives a traumatic episode, the memory is recalled and for a short period of time it is labile and susceptible to modification. The approach of the system according to some embodiments of the present disclosure is to record brain activity during times when the subject is feeling safe and well (i.e., during relaxed state 300). Then, when the subject is experiencing a traumatic episode during waking, this "antidote" pattern 304 can be recreated by using safe, low-level high-definition transcranial current stimulation, thereby interfering with reconsolidation of the traumatic memory.

Below is a description of the procedure and apparatus, and how the stimulation parameters required to recreate the non-trauma pattern (i.e., the antidote pattern 304) are determined. In addition, an automated sleep therapy 318 method is described to recognize the traumatic pattern 308 during stage 4 of non-REM sleep (i.e., slow-wave sleep (SWS)), and automatically invoke the application of a temporally compressed version of the antidote pattern 316, again to break up the consolidation of the traumatic memory across the neocortex.

Figure 4:
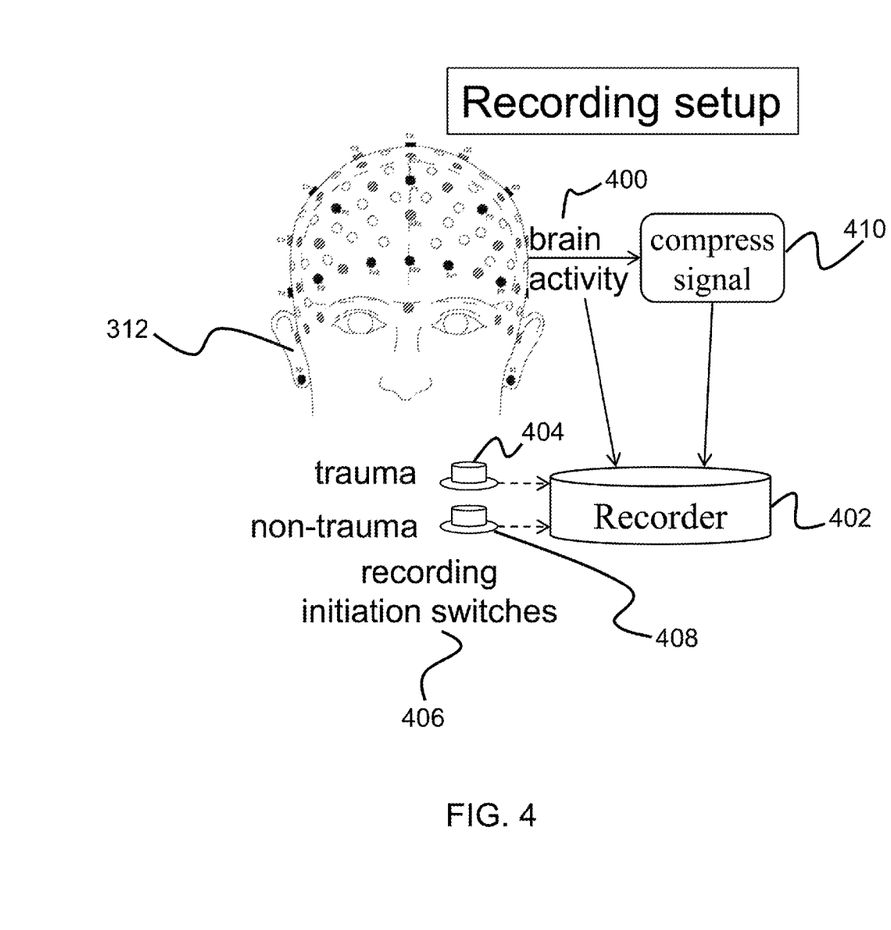
FIG. 4 is an illustration of a recording setup according to various embodiments of the present disclosure.

FIG. 4 depicts the recording setup according to various embodiments of the present invention. The subject 312 notifies the system by initiating a recording of spatiotemporally distributed brain activity 400 from the sensors to a recording device (recorder 402) during the most intense part of the traumatic episode (trauma 404) via, for instance, a recording initiation switch 406 (or button). The traumatic memories (trauma 404) could also be evoked by a sort of psychological questioning in a clinical setting, or if a wearable version of the device is developed, the subject 312 could just wear it and activate it to capture the traumatic episodes (trauma 404) when they occur naturally during the day. Likewise, the recorder 402 can record non-trauma 408 memories to record the antidote pattern 304. The brain activity 400 is converted into a compressed signal 410. There may be two separate recording initiation switches 406 for trauma 404 and non-trauma 408, as shown in FIG. 4.

During recording, waking neo-cortical activity (i.e., brain activity 400) from the subject 312 is converted into a temporally compressed form (compressed signal 410) (using, for instance, a generic compression factor of six to seven as described in Literature Reference No. 12) to use as a cortical replay template that can be matched with activity during deep sleep. During sleep, the antidote pattern 304 must be compressed 316, because when memories are replayed during non-REM sleep, it is at a 6-7 times faster rate than waking recall. Cortical replay occurs at a faster rate than the waking experience. Individual subjects may have different cortical replay rates (as described in Literature Reference Nos. 12 and 13), so cortical replay is adjusted up and down to find the best match. A number of examples of traumatic episodes (trauma 404) should be captured/recorded in order to construct a representative or canonical traumatic episode pattern 308.

Figure 5:
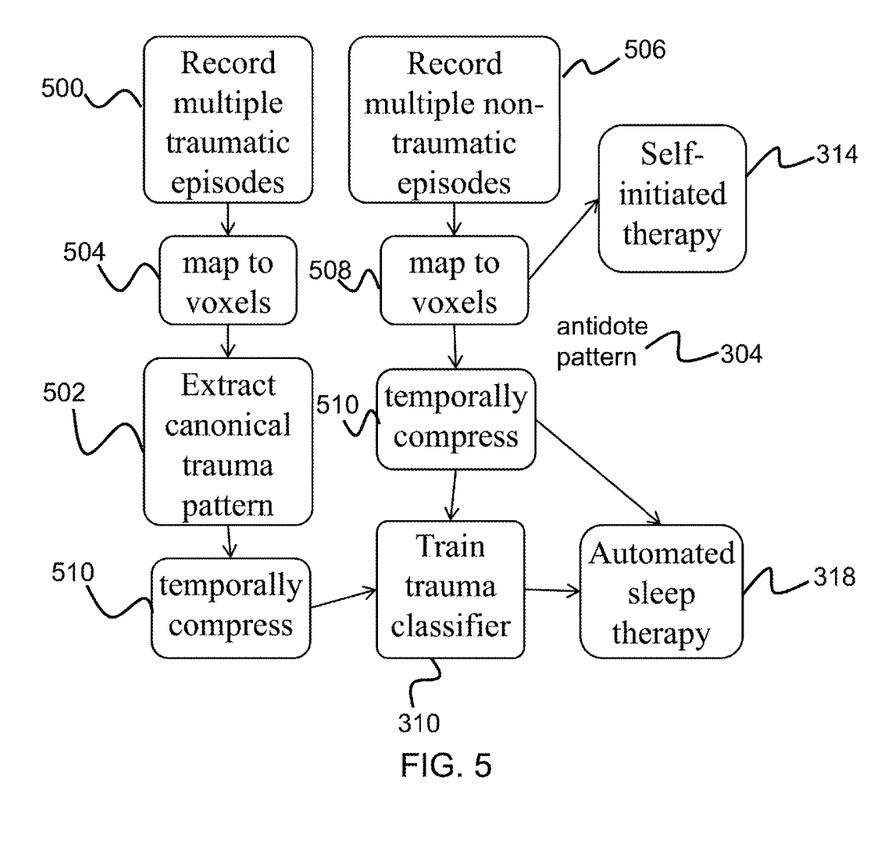
FIG. 5 is an illustration of a waking therapy setup according to various embodiments of the present disclosure.

As shown in the flow diagram depicted in FIG. 5, a subject initiates a recording session to record multiple traumatic episodes 500 at times when a traumatic episode is relived intensely. To extract a canonical trauma pattern 502 from multiple recordings of traumatic episodes, the recordings (signals obtained from the transcranial sensors) must first be mapped to voxels 504 of activity in the brain. Computing the neural activity in areas of the brain volume based on transcranial sensor data (EEG and/or fNIRS) is a problem known in the art as blind source separation, which discovers the most likely sources of the activity recorded from scalp electrodes. Then, the activity in each voxel is averaged between episodes, and voxels with low activity are quenched (i.e., set voxels with less than 10% of the highest voxel activity to zero).

Likewise, the subject records a number of experiences at good times (i.e., record multiple non-traumatic episodes 506), when feeling happy and safe. To ensure that the recordings are maximally different than a traumatic episode, the subject prepares by, for example, doing some relaxation exercises, being in an environment the subject finds restful, and/or doing visualizations. These recordings are mapped to voxels 508, as in the traumatic episode described above. This is the antidote pattern, and it is stored both in uncompressed form (uncompressed antidote pattern 600) for waking therapy as shown in FIG. 6, and temporally compressed form (compressed antidote pattern 700) for sleep therapy, as shown in FIG. 7.

Figure 6:
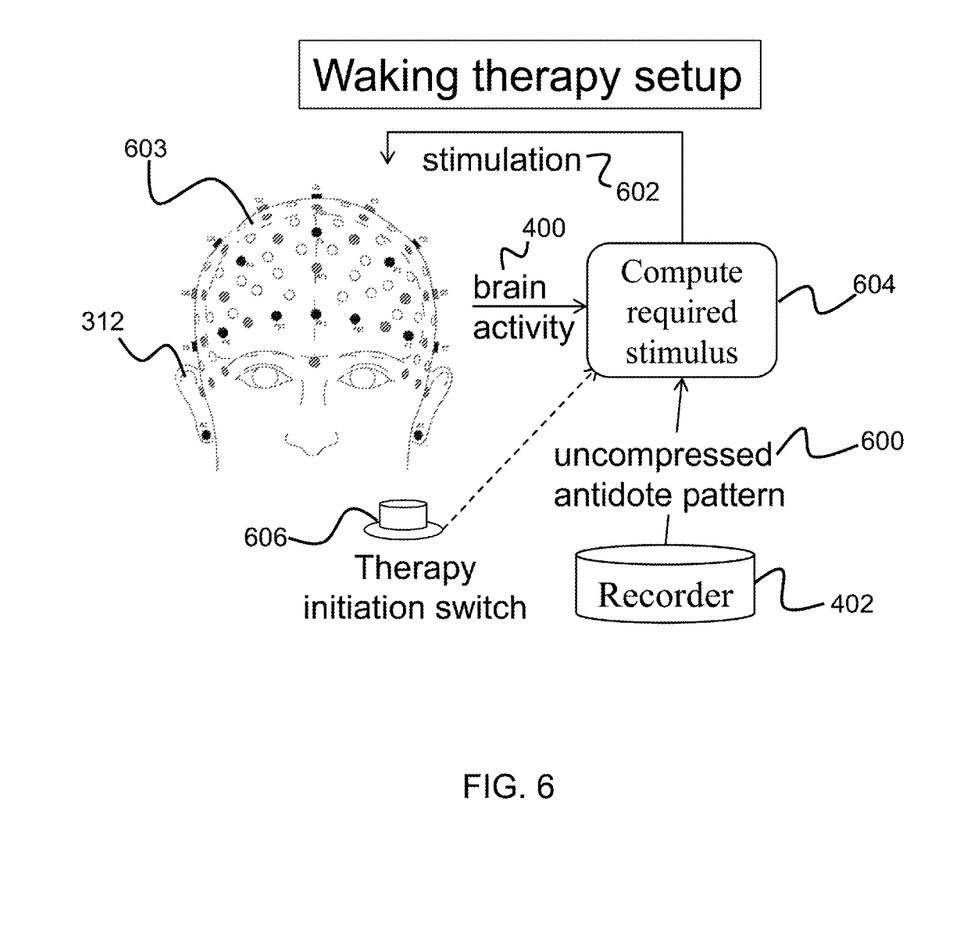
FIG. 6 is a flow diagram illustrating the ordering of procedures leading to two types of therapy according to various embodiments of the present disclosure.

FIG. 6 illustrates the waking therapy setup according to various embodiments. An antidote pattern 304 is recorded (as depicted in FIG. 4) and stored in the recorder 402 as an uncompressed antidote pattern 600. Then, any time the patient/subject 312 relives the traumatic memory during waking, he/she can initiate therapeutic stimulation 602 (i.e., apply the uncompressed antidote pattern 600 via a transcranial stimulation cap 603) based on a computed required stimulus 604 that will interrupt the reconsolidation of the memory via, for example, a therapy initiation switch 606. Each episode with stimulation-based treatment will weaken the memory further.

Figure 7:
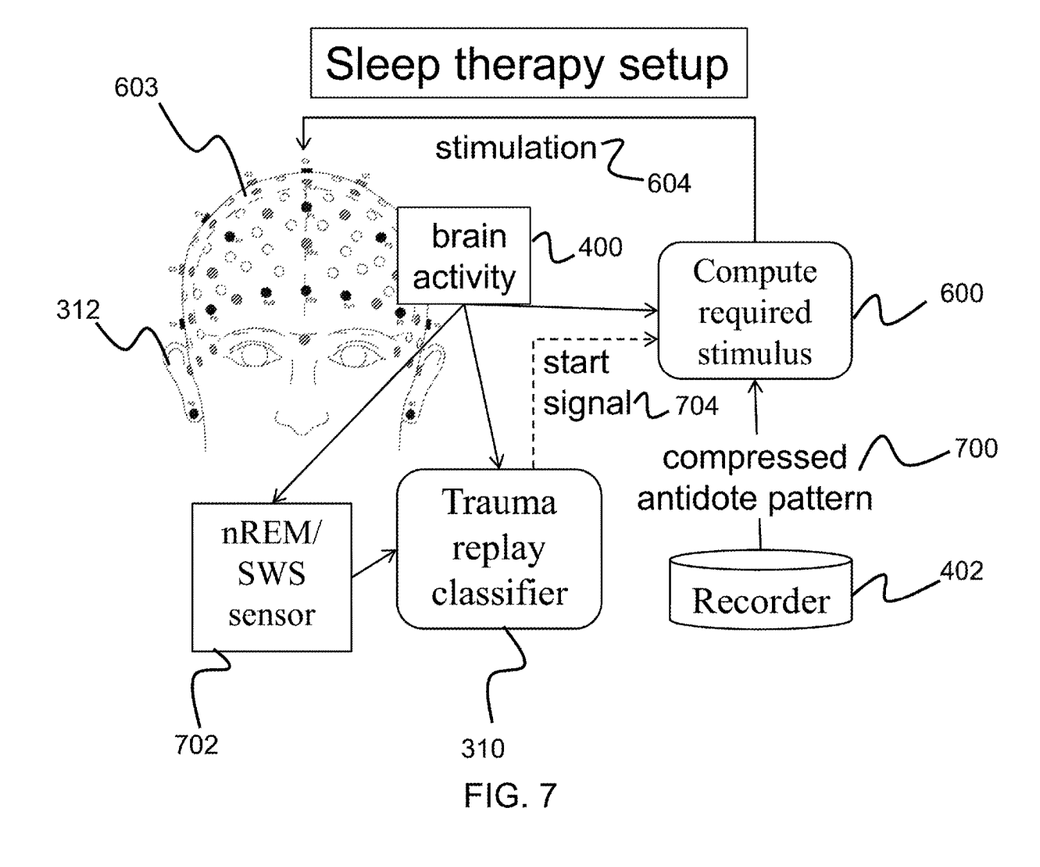
FIG. 7 is an illustration of a sleeping therapy setup according to various embodiments of the present disclosure.

FIG. 7 illustrates a setup for sleep therapy according to various embodiments. During sleep, sensors 702 are used to recognize the traumatic pattern 308 during stage 4 of non-REM sleep (i.e., slow-wave sleep (SWS)) in the subject 312, and automatically invoke the application of a temporally compressed antidote pattern 700 via the transcranial stimulation cap 603. The set of compressed recordings (i.e., brain activity 400) translated to voxels (as depicted in FIG. 5) in the salient set can be used as training examples (i.e., to train a trauma classifier 310), each marked as belonging to one of two categories (trauma and non-trauma). For traumatic memory replay detection during non-REM sleep, the system according to various embodiments of the present invention could use any of several types of classifiers known to those skilled in the art, a non-limiting example of which includes a Support Vector Machine (SVM).

A SVM training algorithm builds a model that assigns new examples into one category or the other, making it a non-probabilistic binary linear classifier. Once the classifier 310 is trained, automated sleep therapy 318 is possible. The subject 312 will sleep wearing the sensor/stimulator array 800 shown in FIG. 8. The classifier 310 will compare brain activity 400 with the compressed version of the canonical trauma pattern during slow-wave sleep (stage 4 of non-REM sleep). When there is a close match, the classifier 310 will initiate (via start signal 704) a treatment using a stimulation montage controller, which will apply the temporally compressed antidote pattern 700 to the stimulation 604 array, weakening a new round of consolidation of the traumatic memory across the neocortex. It is necessary to find a stimulation montage that will reproduce an antidote activity pattern across the brain.

External brain sensors, such as electroencephalogram (EEG), receive signals from the scalp that indicate activity on the surface of the brain. It has long been recognized that the EEG can be analyzed to infer the activity in the three-dimensional (3D) volume of the brain that could have caused the particular surface signals sensed by EEG, using topographic maps and spatial pattern analysis methods as well as source localization techniques (see Literature Reference No. 17). Non-invasive (transcranially applied) electrical stimulation of the brain has been shown in prior art to modulate neuronal activity and synchrony across multiple brain areas and, thereby, to enhance various behaviors.

Described herein is a technique to compute a stimulation montage that can be applied by transcranial stimulation electrodes to reproduce a brain state that was previously sensed by EEG and/or functional near infrared sensing (fNIRS). This requires mapping the externally sensed signals to the most likely set of 3D sources of activity in the brain and then computing an electrical stimulation montage required to transform the current brain state into the desired brain state. The system according to embodiments of the present disclosure uses diffusion tensor imaging (DTI) data to link EEG sources with stimulation-induced current flows in the brain volume, which are different modalities. DTI provides average orientation and density of white matter tracts in each voxel, which are used to convert induced electric fields into neural activity changes.

Based on T1- and T2-weighted magnetic resonance images (MRIs) of a human subject, finite element modeling is used to build a personalized forward model of voltage fluctuations recorded at the EEG/fNIRS electrodes on the scalp (as described in Literature Reference No. 14), as well as a personalized forward model of transcranial stimulation (tCS)-induced current density distributions in the brain volume (see Literature Reference No. 15 for a description of tCS-induced current density distributions). Multi-scale geodesic Sparse Bayesian Learning is used with a Laplacian prior for subject-specific inverse modeling to localize the distributed sources for the transcranially recorded EEG/fNIRS signals (see Literature Reference No. 16).

To determine the stimulation required to reproduce a particular activity pattern across the neocortex, the difference in activity for each voxel of the brain between the desired activity pattern and the current pattern was first computed. Based on diffusion tensor imaging (DTI) data of the subject, which provides fine-grained information on the white matter fiber orientation and density, one can compute the necessary electric field to achieve the desired activity change in each voxel. With the volumetric distribution of desired electric fields within the brain and the material properties of the scalp electrodes, as well as various tissue category masks in the brain volume, any of several types of optimization techniques can be employed to solve for the stimulation montage (such as the technique described in Literature Reference No. 15).

A point neuron activation function models the electrophysiological properties of real neurons, while simplifying their geometry to a single point. The neural activity S tends to increase linearly as a function of applied negative current I (i.e., the current out of a neuron, which moves negative charges away and increases positive potential). If one assumes the gain factor G stays constant during application of the stimulation, and the activity change desired in a particular voxel is $\Delta S$, then the amount of current that needs to be applied along the axis of the neurons in the voxel is $$I = \frac{\Delta S}{G}.$$

To determine the gain factors of various voxels for a given subject, one embodiment of the present disclosure is to arrive at them by applying various stimulation montages and measuring the corresponding affected activity changes across the brain volume. The gain factors in each voxel need to be scaled by the cosine of the angle between the dominant white matter tract orientation and the induced electric field. One skilled in the art can perform this procedure in a straightforward manner.

The procedure is summarized below. Steps 1-4 below create a model of desirable brain activity in the relevant voxels of the brain. This is a prerequisite to using the model to compute required brain stimulations to recreate a desired brain state. One example of a desired brain state is a state in which the subject's behavioral response to a certain experience is either enhanced or reduced. For instance, it could be beneficial to become more sensitive to threats of certain types. In the case of post-traumatic stress disorder, it is desirable to reduce anxiety triggered by certain benign events. Another non-limiting example is to enhance memory function in a person whose brain is improperly storing and recalling memories. In particular, step 2 must be done when the subject is in a desired brain state. For instance, in the case of post-traumatic stress disorder (PTSD), it is desirable to reduce anxiety triggered by certain benign events. Therefore, the desired brain state for a PTSD patient is one in which the subject is calm with low anxiety. Such a brain state can be achieved when the patient is in a quiet, safe place. Breathing exercises together with yoga or meditation are known to lower stress and may be used. Alternatively, calming videos such as the ones used by some airlines to settle passengers down before a long trip (e.g., wildlife scenes accompanied by relaxing music) may also be used.

1. Take T1- and T2-weighted MRIs and a DTI of the subject (as described in detail in Literature Reference No. 18).
2. During a desired brain state, record brain activity using EEG/fNIRS electrodes on the scalp.
3. Use finite element modeling based on the MRIs of step 1 to build a personalized forward model that describes how, for this subject, neural activity in the voxels of the brain create electrical signals that can be sensed on the surface of his skull, as described in Literature Reference No. 14.
4. Use multi-scale geodesic Sparse Bayesian Learning with a Laplacian prior for subject-specific inverse modeling to localize the distributed sources for the transcranially recorded (in step 2) EEG/fNIRS signals of the desired brain state, as described in Literature Reference No. 16. This provides desired activities in each voxel of the brain volume. In many cases, only a few brain regions are relevant for a particular use, the voxels can now be limited to a "relevant set".
5. Subsequently, once steps 1-4 are completed, and when the subject is in an undesirable brain state, record brain activity as in step 2.
6. Repeat step 4 for the undesired brain state.
7. Compute the difference in activity for each relevant voxel of the brain between the desired activity pattern and the current pattern.
8. Translate the desired activity change in each voxel into the necessary electric field, properly aligned to the orientation of the nerve fibers based on DTI data, to achieve the desired activity pattern.
9. With the volumetric distribution of desired electric fields within the brain, and the material properties of the scalp electrodes as well as various tissue category masks in the brain volume having been characterized, an optimization technique is employed to solve for the stimulation montage to create the desired activity change of step 8, analogous to beam-forming but imposing additional limits on the maximum injected current due to safety. In one embodiment, the optimization technique described in Literature Reference No. 15 is implemented. However, as can be appreciated by one skilled in the art, additional suitable methods exist that could be used to solve for the stimulation montage.
10. With the volumetric distribution of desired electric fields within the brain, and the material properties of the scalp electrodes as well as various tissue category masks in the brain volume having been characterized, any of several types of optimization techniques are employed to solve for the stimulation montage to create the desired activity change of step 8 (e.g., Literature Reference No. 15).

11. Apply the stimulation montage and repeat steps 5-9 as needed.

Figure 8:
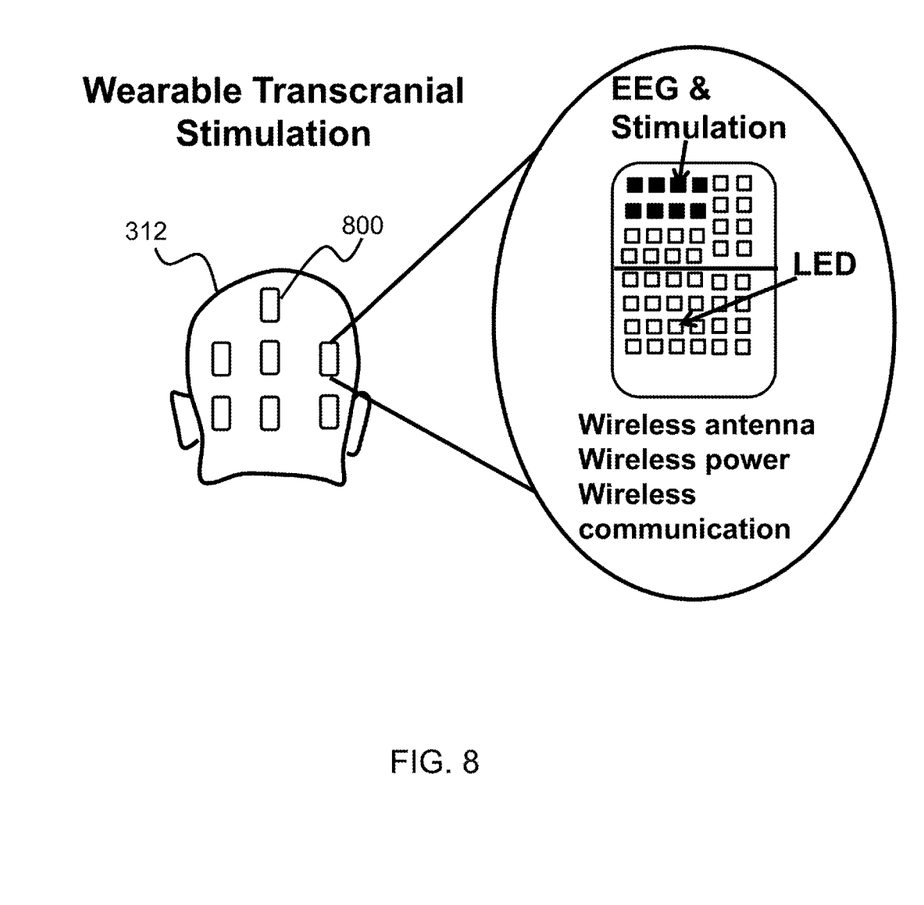
FIG. 8 is an illustration of wearable transcranial stimulation according to various embodiments of the present disclosure.

In each of the setups described herein, the subject 312 wears a high-density array of sensors and stimulators on the head, containing sensors, such as EEG (electro-encephalogram) and fNIRS (functional near-infrared spectroscopy), and electrical stimulators, such as HD-tCS (high-definition tCS). As illustrated in FIG. 8, this sensor/stimulator array 800 comprising a plurality of sensors/stimulators can be engineered in an ergonomic design. For example, MC-10, Inc. makes conformal, nearly invisible, stretchy electronics that could be used in the present invention. MC-10, Inc. is located at 10 Maguire Road Building 3, 1st Floor, Lexington, Mass. 02421. Each array 800 can comprise any of the following: light emitting diode (LED), EEG sensors, and electrical stimulators. Further, the array 500 can include a wireless antenna, wireless power, and wireless communication.

The present invention offers many advantages over the prior art. The therapeutic procedure is safe and does not require any drugs. The system can be self-trained using events when the subject experiences traumatic memories. The therapy can be either self-applied during wake, or automatically applied at night, and does not require supervision by a doctor or a psychological therapist. The therapy is targeted; it is applied only during the reconsolidation period of the traumatic memory (on the order of minutes) compared with a drug treatment whose effects can last for many hours and have unintended systemic chemical side-effects. Additionally, there is no need for the subject to attend frequent and expensive behavioral therapy sessions.

The first state of transition of the present invention could be a clinical system for lab use where the disturbing memory needs to be artificially evoked. A second stage could be a home system that can be either self-initiated or works automatically. A final stage could be a portable personal therapy system that also can be operated by a naïve user with minimal supervision.

What is claimed is:

1. A system for weakening traumatic memories, the system comprising:
    one or more processors and a non-transitory memory having instructions encoded thereon such that when the instructions are executed, the one or more processors perform operations of:
    using magnetic resonance imaging (MRI) data, snapping a first set of transcranial sensor electrical signals of a first brain state to relevant voxels of brain volume, wherein the first brain state occurs indicating a first memory or set of memories;
    using magnetic resonance imaging data, mapping a second set of transcranial sensor electrical signals of a second brain state to relevant voxels of brain volume, wherein the second brain state occurs indicating no recall of the first memory or set of memories;
    determining a difference in activity for each relevant voxel between the first set of transcranial sensor electrical signals and the second set of transcranial sensor electrical signals, resulting in a desired activity change in each voxel;
    translating the desired activity change in each voxel into a desired electric field by using an optimization technique to solve for the desired electric field;
    training a classifier to recognize the first set of transcranial sensor electrical signals associated with the first memory or set of memories; and
    when the classifier recognizes the first set of transcranial sensor electrical signals associated with the first memory or set of memories, then applying, via a set of electrodes, the desired electric field to transition from the first brain state toward the second brain state.

2. The system as set forth in claim 1, wherein recording of the first and second set of transcranial sensor electrical signals is adapted to be initiated by a human subject.

3. The system as set forth in claim 2, wherein the first and second set of transcranial sensor electrical signals are sensed by a high-resolution sensor array that is adapted to be distributed over the head of the human subject.

4. The system as set forth in claim 1, wherein the one or more processors perform operation of:
    recognizing, with the trained classifier, a neocortical replay associated with the first set of transcranial sensor electrical signals while a human subject is asleep; and
    initiating therapy automatically, applying transcranial electro-stimulation corresponding to the desired electric field at the set of electrodes.

5. The system as set forth in claim 1, wherein the one or more processors further perform an operation of applying transcranial electro-stimulation corresponding to the desired electric field at the set of electrodes when a human subject is awake.

6. The system as set forth in claim 1, wherein the desired electric field is applied using a transcranial stimulation cap adapted to be worn by a human subject.

7. The system as set forth in claim 1, wherein using diffusion tensor imaging (DTI) data, linking at least one of electroencephalogram (EEG) and functional near infrared sensing (fNIRS) signals with stimulation-induced flows in brain volume, wherein DTI provides average orientation and density of white matter tracts in each voxel, which are used to convert electric fields into the desired activity change.

8. The system as set forth in claim 1, wherein the one or more processors further perform operations of:
    using weighted MIll data of a human subject, generating a personalized model of voltage fluctuations in the transcranial sensor electrical signals; and
    generating a personalized model of transcranial stimulation (tCS)-induced current density distribution in brain volume.

9. The system as set forth in claim 1, wherein using diffusion tensor imaging (DTI) data, the desired activity change in each voxel is translated into the desired electric field by aligning to an average orientation of white matter tracts in each voxel.

10. The system as set forth in claim 1, wherein the desired electric field is generated using a stimulation montage.

11. A computer-implemented method for weakening traumatic memories, comprising:
    an act of causing one or more processors to execute instructions stored on a non-transitory memory such that upon execution, the one or more processors perform operations of:
    using magnetic resonance imaging data, mapping a first set of transcranial sensor electrical signals of a first brain state to relevant voxels of brain volume, wherein the first brain state occurs indicating a first memory or set of memories;
    using magnetic resonance imaging (MRI) data, mapping a second set of transcranial sensor electrical signals of a second brain state to relevant voxels of brain volume, wherein the second brain state occurs indicating no recall of the first memory or set of memories;

determining a difference in activity for each relevant voxel between the first set of transcranial sensor electrical signals and the second set of transcranial sensor electrical signals, resulting in a desired activity change in each voxel;

translating the desired activity change in each voxel into a desired electric field by using an optimization technique to solve for the desired electric field;

training a classifier to recognize the first set of transcranial sensor electrical signals associated with the first memory or set of memories; and when the classifier recognizes the first set of transcranial sensor electrical signals associated with the first memory or set of memories, then applying, via a set of electrodes, the desired electric field to transition from the first brain state toward the second brain state.

12. The method as set forth in claim 11, wherein a human subject initiates recording of the first and the second set of transcranial sensor electrical signals.

13. The method as set forth in claim 12, wherein the first and second set of transcranial sensor electrical signals are sensed by a high-resolution sensor array distributed over the head of the human subject.

14. The method as set forth in claim 11, wherein the one or more processors perform operations of:

recognizing, with the trained classifier, a neocortical replay associated with the first set of transcranial sensor electrical signals while a human subject is asleep; and initiating therapy automatically, applying transcranial electro-stimulation corresponding to the desired electric field at the set of electrodes.

15. The method as set forth in claim 11, wherein the one or more processors further perform an operation of applying transcranial electro-stimulation corresponding to the desired electric field at the set of electrodes when a human subject is awake.

16. The method as set forth in claim 11, wherein the desired electric filed is applied using a transcranial stimulation cap worn by a human subject.

17. A computer program product for weakening traumatic memories, the computer program product comprising:

computer-readable instructions stored on a non-transitory computer-readable medium that are executable by a computer having one or more processors for causing the processor to perform operations of:

using magnetic resonance imaging data, mapping a first set of transcranial sensor electrical signals of a first brain state to relevant voxels of brain volume, wherein the first brain state occurs indicating a first memory or set of memories;

using magnetic resonance imaging (MRI) data; mapping a second set of transcranial sensor electrical signals of a second brain state to relevant voxels of brain volume, wherein the second brain state occurs indicating no recall of the first memory or set of memories;

determining a difference in activity for each relevant voxel between the first set of transcranial sensor electrical signals and the second set of transcranial sensor electrical signals, resulting in a desired activity change in each voxel;

translating the desired activity change in each voxel into a desired electric field by using an optimization technique to solve for the desired electric field;

training a classifier to recognize the first set of transcranial sensor electrical signals associated with the first memory or set of memories; and when the classifier recognizes the first set of transcranial sensor electrical signals associated with the first memory or set of memories, then applying, via a set of electrodes, the desired electric field to transition from the first brain state toward the second brain state.

18. The system as set forth in claim 17, wherein recording of the first and second set of transcranial sensor electrical signals is adapted to be initiated by a human subject.

19. The system as set forth in claim 18, wherein the first and second set of transcranial sensor electrical signals are sensed by a high-resolution sensor array that is adapted to be distributed over the head of the human subject.

20. The computer program product as set forth in claim 17, further comprising instructions for causing the one or more processors to perform operations of:

recognizing, with the trained classifier, a neocortical replay associated with the first set of transcranial sensor electrical signals while a human subject is asleep; and initiating therapy automatically, applying transcranial electro-stimulation corresponding to the desired electric field at the set of electrodes.

21. The computer program product as set forth in claim 17, further comprising instructions for causing the one or more processors to further perform an operation of applying transcranial electro-stimulation corresponding to the desired electric field at a set of electrodes when a human subject is awake.

* * * * *